United States Patent [19]

Mitchell et al.

[11] Patent Number: 4,876,096

[45] Date of Patent: * Oct. 24, 1989

[54] RICE SYRUP SWEETENER

[75] Inventors: Cheryl R. Mitchell; Pat R. Mitchell, both of Manteca, Calif.; William A. Mitchell, Shelburne, Vt.

[73] Assignee: California Natural Products, Manteca, Calif.

[ * ] Notice: The portion of the term of this patent subsequent to Jul. 12, 2005 has been disclaimed.

[21] Appl. No.: 174,598

[22] Filed: Mar. 29, 1988

Related U.S. Application Data

[62] Division of Ser. No. 856,504, Apr. 28, 1986, Pat. No. 4,756,912.

[51] Int. Cl.$^4$ .......................... A23L 1/09; A23L 1/05
[52] U.S. Cl. ........................................ 426/28; 426/44; 426/52; 426/61; 426/618; 426/650; 426/658
[58] Field of Search ........................ 426/18, 28, 29, 48, 426/44, 50, 61, 51, 52, 618, 656, 640, 598, 599, 658, 534, 650; 435/94, 95, 96, 99

[56] References Cited

U.S. PATENT DOCUMENTS

| | | | |
|---|---|---|---|
| 3,644,126 | 2/1972 | Bodnar et al. | 426/48 |
| 4,235,965 | 11/1980 | Walon | 426/48 |
| 4,282,319 | 8/1981 | Conrad | 426/28 |
| 4,285,975 | 8/1981 | Glenister | 426/29 |
| 4,756,912 | 7/1988 | Mitchell et al. | 426/28 |

Primary Examiner—Marianne Cintins
Attorney, Agent, or Firm—John A. Bucher

[57] ABSTRACT

Whole grain rice, either white or brown rice, is liquefied and treated with high levels of a glucosidase enzyme and/or a combination with beta-amylase enzyme in a saccharification step. Total enzymatic reaction time is limited to about four hours for both the liquefaction and saccharification steps combined to prevent the development of undesirable off-flavors. The product of the saccharification step is partially clarified to remove substantially all rice fiber, but not other nutritional values and then concentrated to produce a preferred rice syrup sweetener which is cloudy in character and has a solids composition defined as follows:

| | |
|---|---|
| Soluble Complex Carbohydrates | About 10 to 70% of solids; |
| Maltose | About 0 to 70% of solids; |
| Glucose | About 5 to 70% of solids; |
| Ash or Minerals | About 0.1 to 0.6% of solids; |
| Protein and Fat | About 1 to 3.5% of solids; |

The rice syrup sweetener of the invention can be dried to produce dried rice sweeteners.

15 Claims, No Drawings

4,876,096

RICE SYRUP SWEETENER

This application is a division of application Ser. No. 06/856,300, now U.S. Pat. No. 4,756,912, filed Apr. 28, 1986.

FIELD OF THE INVENTION

The present invention relates to an enzymatic method for producing a cloudy, hypo-allergenic and nutritious rice syrup sweetener which can be used either as a beverage or in a variety of food products as well as a product of the method.

BACKGROUND OF THE INVENTION

Clarity has been generally considered one of the prime requirements in prior art commerical syrups or sweeteners such as corn syrup, maple syrup, and sorghum syrup. In the normal preparation of syrup from grain, for example, corn syrup from corn grain, the starch component is first separated from the grain. This initial separation or removal of fat, protein, cellulose, color and flavor bodies from the grain prevents those components from interfering with or inhibiting preparation of the syrup.

In the separation of starch from the corn grain, sulfur dioxide is commonly used which to some degree remains in the starch and finds its way into the final syrup as an undesirable constituent.

More particularly, many of the above mentioned constituents interfere with starch dextrinizing or liquefaction and saccharification action. Tha bove mentioned difficulties are such that most commercial syrups are made from a recovered or separated starch component of the grain. The liquefaction and saccharification reactions are usually carried out over extended periods of time, for example, six to twenty-four hours or longer.

Recently, increased commercial interest has developed in nutritional syrups which, in addition to sweetness from sugars such as maltose and glucose, also include nutritional factors such as proteins, minerals and complex carbohydrates which are usually removed in normal syrup production.

However, with grain products of the type referred to above, many people have demonstrated allergic reactions particularly to cereal grains such as corn and wheat as well as products derived from those grains.

Accordingly, there has been found a need for a low allergenic syrup or sweetener which can be used in place of sweeteners of the type described above. At the same time, there is a need or a commercial market for such syrups or sweeteners which retain a relatively high level of nutritional factors while also containing acceptable levels of sugars such as maltose and glucose to achieve a suitable sweetening effect.

Another invention set forth separately entitled Nutritional Rice Milk Product and Method of Production, filed contemporaneously with the present case in an application co-pending with the above noted parent, 06/856,300 filed Apr. 24, 1966, now U.S Pat. No. 4,744,992; entitled NUTRITIONAL RICE MILK PRODUCTION and assigned to California Natural Products is related to the present invention and is accordingly incorporated herein by reference as though set forth in its entirety. The above noted reference involves rice milk or modified amazake products which are formed by generally the same steps employed for the rice syrup sweetener product of the present invention. However, as a final step, the rice syrup sweeteners of this invention are partially clarified, preferably by sieving and centrifuging in order to remove substantially all rice fiber. That reference is accordingly incorporated herein to the extent that it may be of assistance in disclosing and facilitating a further understanding of the present invention.

SUMMARY OF THE INVENTION

It is an object of the present invention to provide a nutritional, non-allergenic rice syrup sweetener which can readily be used in place of many commercial syrups or sweeteners as described above while also providing a method for producing the rice syrup sweetener. More preferably, the rice syrup sweetener of the invention has a cloudy character or appearance due to the presence of nutritional factors including minerals, proteins and fat.

It is a further related object of the invention to provide such a rice syrup sweetener which is produced by a method employing whole grain rice as a starting material. The rice syrup sweetener of the invention is produced from ground white or brown rice, for example, by liquefaction or dextrinization of steamed or cooked rice to form a liquefied slurry which is then reacted with relatively high levels of glucosidase enzyme either alone or in combination with a beta-amylase enzyme to produce a rice syrup sweetener having various desired characteristics. More preferably, the saccharification step is carried out with from about 440 to 2,200 Diazyme Units of a glucosidase enzyme per kilogram of whole grain rice with optionally a beta-amylase enzyme from about 1,000 to 3,000 DP° per kilogram of whole grain rice. The amount and/or proportions of the glucosidase enzume alone or in combination with the beta-amylase enzyme can be varied according to the present invention to produce rice syrup sweeteners having varying concentratins of components, particularly maltose and glucose. Accordingly, the solids composition of the rice syrup sweetener of the invention is as follows:

| Soluble Complex Carbohydrates | About 10 to 70% of solids; |
| --- | --- |
| Maltose | About 0 to 70% of solids; |
| Glucose | About 5 to 70% of solids; |
| Ash or Minerals | About 0.1 to 0.6% of solids; |
| Proteins and Fat | About 1 to 3.5% of solids. |

From the above composition, it may be seen that the non-carbohydrate nutritional elements of the rice syrup sweetener include ash or minerals, protein and fat, forming about 1.1 to 4.1% of solids in the composition.

Following the saccharification step referred to above, the saccharification product is partially clarified to remove substantially all rice fiber and then concentrated so that the finished rice syrup sweetener preferably comprises from about 70 to 82% soluble solids.

The concentration of glucosidase enzyme and the concentration of optionally employed beta-amylase enzyme in the saccharification step are set forth respectively in Diazyme Units and DP°. These standards are employed with the following explanation to assure a proper understanding of the invention. In that regard, the term "DP°" refers to Degrees of Diastic Power. A further definition as well as an extensive assay procedure in connection with that term is set forth for example in *Food Chemicals Codex,* third edition, beginning at page 484.

The term "Diazyme Units" refers to a Diazyme assay commercially available from Miles Laboratories, Inc., Elkhart, Ind. That term is employed herein at least partially since one glucosidase enzyme found suitable for use in the present invention comprises glucoamylase E.C. 3.2.1.3, 1, 4 - alpha - D-Glucan Glucohydrolase, unit activity of about 200 Diazyme Units/ml. (available under the trade name Diazyme from Miles Laboratories, Inc., Elkhart, Indiana).

It is yet a further object of the invention to concentrate the rice syrup sweetener to include about 70 to 82% solids as noted above. However, it is an even further object of the invention to form a dried version of the rice syrup sweetener which can be employed either in its dried form or stored and later reconstituted for example to form a rice syrup sweetener with approximately 70 to 82% solids as noted above.

It is a still further object to provide a rice syrup sweetener using whole grain rice as a starting material and employing a beta-amylase enzyme of at least 1,000 DP° per kilogram of whole grain rice in a saccharification step limited to about three hours. This process has been found to yield a high maltose rice syrup sweetener which is nutritional and non-allergenic while also being characterized by freedom from a rice-like flavor and a cloudy appearance because of the nutritional values remaining from the whole grain rice starting material.

Substantially greater amounts of the beta-amylase enzyme may be used if desired. However, it has generally been found to be preferred to use about 1,000 to 3,000 DP° of beta-amylase per kilogram of whole grain rice to economically achieve the advantages of the invention. This high maltose rice syrup sweetener may also be converted to a dried product.

In connection with the present invention, additional objects and advantages referred to in the specification incorporated above by reference are also of importance in connection with the present invention.

Additional objects and advantages of this invention are also made apparent in the following description.

DESCRIPTION OF THE PREFERRED EMBODIMENT

As in the incorporated reference set forth above, the rice syrup sweetener of the present invention is formed by initially selecting whole grain rice, either white rice (polished) or brown rice (unpolished). Preferably, the rice is ground or divided to form particles of from about 10 to 60 mesh.

The ground rice particles are liquefied or dextrinized preferably in a water slurry by treatment with an alphaamylase enzyme at 30–100°C. where the enzymatic reaction duration for the liquefaction step is limited to about one hour to prevent development of undesirable off-flavors.

The liquefied slurry is then saccharified with relatively high levels of a glucosidase enzyme either alone or in optional combination with a variable amount of betaamylase enzyme to produce a solids composition as set forth above.

The saccharified product is then partially clarified to remove substantially all rice fibers while leaving substantially all other nutritional values including ash or minerals, protein, fat, vitamins, etc. in the partially clarified product which can then be concentrated, preferably to about 70 to 82% solids. As noted above, the rice syrup sweetener of the invention may also be dried to form a dried syrup or sweetener which is non-allergenic and still contains many of the nutrient values referred to above. The dried syrup or sweetener may either be used in its dried form in various food products or it may be stored and later reconstituted to form the rice syrup sweetener referred to above.

Additional preferred features of the process and product of the invention are set forth below. Prior to the statement of examples illustrating both the method and product of the invention.

As noted above, the process of the invention includes whole grain rice as a starting material with reaction conditions such as temperature, pH, time of reaction, type and concentration of enzyme being particularly selected to result in the desirable rice syrup sweetener referred to above.

In particular, it has been discovered that a high level of saccharifying enzyme and a relatively limited enzymatic reaction time or duration of about to two to four hours (for both liquefaction and saccharification) are required to produce the rice syrup sweetener of the invention. These limitations result in a rice syrup sweetener which is nutritious and generally free from a rice-like flavor. At the same time, the nutritional values remain in the rice syrup sweetener from the whole grain rice starting material.

The saccharification step preferably employs a glucosidase enzyme, for example, a glucoamylase, E.C.3.2.1.3 1,4-alpha-D-Glucan having a unit activity of 200 Diazyme Units per ml and available for example under the trade name Diazyme from Miles Laboratories, Inc., Elkhart, Indiana. Similar glucosidase enzymes are commercially available for example from Novo Industries of Denmark and from The FinnSugar Group of Finland. Preferably, from about 440 to about 2,200 Diazyme Units of the glucosidase enzyme are employed in the saccharification step per kilogram of whole grain rice particles.

The glucosidase enzyme referred to above may be employed either alone in the saccharification step or in combination with a beta-amylase enzyme having an activity from about 1,000 to 3,000 DP° per kilogram of whole grain rice as defined above. The amounts of the glucosidase enzyme and optional amounts of beta-amylase enzyme may be varied in order to produce rice syrup sweeteners having the composition referred to above. Additional details concerning these enzymes are set forth in the above incorporated reference.

In the dextrinizing or liquefaction step, the alphaamylase enzyme is preferably employed at levels of from 2,400,000 to 3,600,000 modified Wohlgemuth Units (modified Wohlegmuth method assembly, Miles Laboratories, Inc., Elkhart, Indiana 46514).

Preferably, the enzymatic reaction time for the liquefaction step is limited to about one hour and the enzymatic reaction time for the saccharification step is limited to about two to three hours. In this manner, desired enzymatic conversion is permitted within the respective steps while preventing undesirable development of off-flavors due for example to rancidity and enzyme activity on the non-starch fractions of the rice. The shortened reaction times for the liquefaction and saccharification steps also minimizes undesirable bacterial action which sometimes takes place with longer reaction times.

The saccharification reaction is preferably carried out at about the normal pH of rice (about 6.3) or in a preferred range of 6 to 6.5. However, it is also possible for the saccharification step to be carried out with an adjusted pH for example in the range of about 3.5 to 7. Such a broad range of pH level may be desirable to enhance enzyme activity under certain conditions.

After completion of the saccharification reaction or step, the saccharification product or slurry is sieved through a 100 mesh sieve or screen and the resulting solution is centrifuged in a partial clarification step.

The partially clarified product is then concentrated, preferably under vacuum conditions at about 71° C. to form the resulting rice syrup sweetener with a solids concentration of about 70 to 82% (soluble solids). As noted above, the rice syrup sweetener is characterized by a cloudy nature or color.

The rice syrup sweetener can be further dried to remove substantially all water in order to form a dried syrup or sweetening agent which is similarly non-allergenic while being characterized by many of the advantageous features referred to above. The dried sweetener is commonly referred to as a sugar and may be employed either in its dried form or stored and later reconstituted to form a liquid rice syrup sweetener as described above. To more particularly described the various enzyme systems, the dextrinization or liquefaction step is preferably carried out with enzymes having alpha-amylase activity common for example to microorganisms such as Bacillus subtilis and Bacillus licheniformis or a fungal source such as Aspergillus oryzae. The enzymes can be used in a pH range of from about 3.5 to 7.5 and at a temperature range of from about 30° C. to 100° C.

The saccharification step is carried out with a glucosidase enzyme either alone or in combination with a beta-amylase enzyme. Such glucosidase enzymes are typically produced by microorganisms selected from Rhizopus or *Aspergillus niger*, *Aspergillus oryzae*, Mucor species, Endomyces Species, *Endomyces fibuliger*, Chlostridum and Acetobutylicum. Beta-amylase enzymes are typically extracted from the following grains: barley, wheat, rye, sweet potato or soy beans.

The rice syrup sweetener produced by the invention can be used in generally the same manner as commercial corn sweeteners or other similar syrups and sweeteners. However, it is again noted that the rice syrup sweetener of the present invention have a number of special properties. In particular, the fact that the rice syrup sweetener is substantially non-allergenic suggests a number of applications for which the product is particularly suited. The corresponding dried syrup or sweetening agent can also be termed "rice sugar" and can be used as a replacement for normal glucose or sucrose in many applications again noting the preferred advantages of the product of the invention as set forth above.

Having outlined and summarized the method and product of the invention, representative procedures for producing various products according to the ivnention are set forth in the following detailed examples.

EXAMPLE 1

High Maltose Rice Syrup Sweetener

Forty-five kilograms of milled brown rice were sifted through a 30 mesh screen and added to 100 liters of water at 25° C. having a calcium content of 200 ppm. The combination was stirred in a steam jacketed kettle of 225 liter capacity.

One hundred grams of bacterial alpha-amylase of Bacillus subtilis origin having an activity of 1,200,000 modified Wohlgemuth units per gram were added and the temperature of the suspension raised to 80° C. by passing steam through the jacketed kettle. The mixture was held at 80° C. for thirty minutes after which the temperature was raised to 100° C. and held at that level for an additional 15 minutes.

The slurry was cooled to 60° C. and 50 ml. of barley malt beta-amylase, having an activity of 1500 DP° per ml were added along with 100 mls. of glucosidase enzyme, specifically Diazyme, with an activity of 200 Diazyme Units per ml.

The slurry was held at 60° C. for 90 minutes and then sieved or screened through a 100 mesh stainless steel screen and centrifuged to remove remaining insoluble particles, particularly rice fibers. However, as noted above, the screen mesh was selected to pass other nutritional values including ash or minerals, proteins, fat, vitamins, etc.

The solution obtained from the centrifuge was concentrated in a vacuum at 71° C. to a soluble solids content of 77%.

The syrup was characterized by a cloudy nature or appearance and had the following analysis: Dextrose equivalent —42, glucose—8%, maltose—35%, maltotriose-13%, higher complex saccharides—49%, protein—0.6%, ash or minerals—0.4%, carbohydrates—74% total, fat—2.0% (all of the above as a percentage of solids) and moisture or water about 23%. Reaction pH during both liquefaction and saccharification was about 6.3. As noted above, rice fiber was essentially removed in the classification step so that it did not form a component of the resulting cloudy rice syrup sweetener.

EXAMPLE 2

High Glucose Rice Syrup Sweetener

Forty-five kilograms of ground white rice sieved to pass through a 40 mesh screen were placed in a steam jacketed kettle containing 80 liters of water at 25° C containing 100 ppm calcium ion.

To this mixture with constant stirring was added 100 grams of bacterial alpha-amylase of Bacillus subtilis origin with an activity of 1,200,000 modified Wohlgemuth units per gram. The temperature of the stirred slurry was increased to 80° C. and held at that temperature for thirty minutes. The temperature was then raised to 100° C. and the mixture held there for another 15 minutes.

The mixture was cooled to 60° C. and 450 ml. Glucoamylase E.C.3.2.1.3. 1,4-alpha-D-Glucan with a unit activity of 200 Diazyme Units ml. added.

The slurry was held at 60° C. for three hours then sieved through a 100 mesh screen and insoluble particles further separated by centrifugation.

The liquors were concentrated in a vacuum at 71° C. to a soluble solids content of 78%.

The resulting cloudy tan colored syrup had the following analysis: Dextrose Equivalent 57; glucose 32%; maltose 21%; maltotriose 3%, higher complex carbohydrates 42%, protein 0.5%; ash 0.3%; carbohydrates 76.4%; fat 0.8%; moisture 22%. Fiber was essentially absent in the cloudy tan colored syrup.

EXAMPLE 3

Dried Rice Syrup Sweetener or Rice Sugar

The rice syrup sweetener of EXAMPLE 1 was poured into the pinch of a double rotating drum dryer with the temperature of the drum surfaces maintained at about 160° C. The dried rice syrup sweetener or sugar was scraped from the drums with doctor blades and ground in a Stokes Tornado Mill to about 100 mesh forming a mildly sweet, off-white powder having characteristics otherwise as described above.

EXAMPLE 4

High Maltose-Low Glucose Rice Syrup Sweetener

EXAMPLE 1 was repeated except that no glucosidase enzyme was employed in the saccharification step.

This resulted in a high maltose rice syrup sweetener having a dextrose equivalent of about 38, glucose about 3%, maltose about 40% and otherwise having a composition and characteristics similar to the rice syrup sweetener of EXAMPLE 1. In particular, the high maltose rice syrup sweetener was found capable of drying in the same manner set forth in EXAMPLE 3 to yield a dried high maltose rice syrup sweetener.

EXAMPLES 1, 2 and 4 are particularly representative of a variety of products which can be produced according to the present invention and having the range of compositions set forth above in the Summary of the Invention. The resulting rice syrup sweetener can of course be concentrated to a variety of concentrations. In addition, the rice syrup sweetener of the invention may be completely dried as indicated in EXAMPLE 3 to form a dried product or sugar which may for example be used either in its dried form or stored and reconstituted to form a rice syrup sweetener as described above in EXAMPLES 1 and 2.

Additional variations and modifications of the invention are believed obvious in addition to those set forth above. Accordingly, the scope of the invention is defined only by the following appended claims.

What is claimed is:

1. A rice syrup sweetener product formed by a method comprising the steps of
   selecting as a starting material a whole grain rice and dividing it into particles of reduced size,
   liquifying the whole grain rice particles with an alpha-amylase enzyme in an aqueous medium substantially free from protease, in an amount and for a period of time sufficient to form a liquid slurry,
   treating the liquid slurry with a glucosidase enzyme in a saccharification step in an amount and for a period of time less than about three hours for yielding a saccharification product have a glucose of content of about 5 to 70% solids,
   clarifying the saccharification product to remove substantially all rice fiber to form a partially clarified product, and
   concentrating the partially clarified product to produce the rice syrup sweetener product having a protein content on a dry-weight basis of less than about 3.5%, the product being colloidal or non-filtratable.

2. The product of claim 1 wherein about 440 to 2,200 Diazyme Units of glucosidase per kilogram of whole grain rice particles are employed in the saccharification step and up to about 3,000 BP° of beta-amylase enzyme per kilogram of whole grain rice particles are also employed in the saccharification step with the resulting partially clarified product having total solids of at least about 70%, balance essentially water, with a composition of:

| | |
|---|---|
| Soluble complex carbohydrates | about 10 to 70% of solids; |
| Maltose | about 0 to 70% of solids; |
| Glucose | about 5 to 70% of solids; |
| Non-carbohydrate nutritional components | about 1 to 5% of solids; |
| and substantially no fiber. | |

3. The product of claim 2 wherein the concentrating step of the method is selected for reducing the rice syrup sweetener to about 70 to 82% total solids.

4. The product of claim 2 wherein the starting material is selected as whole grain rice particles and the liquifaction, saccharification and clarification steps are selected so that the resulting rice syrup sweetener product has nutritional components comprising ash or mineral at about 0.1 to 0.6% of solids and protein and fat at about 1 to 3.5% of solids.

5. The product of claim 3 wherein the the method further comprises the step of drying the rice syrup sweetener product to substantially remove water and thereby form a dried rice syrup sweetener product.

6. The product of claim 2 wherein the the method further comprises the step of drying the rice syrup sweetener product to substantially remove water and thereby form a dried rice syrup sweetener product.

7. The product of claim 1 wherein the the method further comprises the step of drying the rice syrup sweetener product to substantially remove water and thereby form a dried rice syrup sweetener product.

8. A rice syrup sweetener product formed by a method comprising the steps of
   selecting as a starting material a whole grain rice and dividing it into particles of reduced size,
   combining the whole grain rice particles with an alphaamylase enzyme in a liquifaction step substantially free from protease in an amount sufficient and for a period of time limited in enzymatic reaction duration to about one hour in order to form a liquid slurry while permitting desired enzymatic liquifaction and preventing development of undesirable, rancid, flat-sour flavors,
   treating the liquid slurry with an enzymatic system comprising a glucosidase enzyme of at least about 440 Diazyme Units per kilogram of whole grain rice particles in a saccharification step limited in enzymatic reaction duration to about three hours, the amount of glucosidase enzyme and the enzyme reaction duration being sufficient to permit desired enzymatic reaction while preventing development of undesirable, rancid, flat-sour flavors,
   clarifying the saccharification product to remove substantially all rice fibers to form a partially clarified product, and
   concentrating the partially clarified product to produce the rice syrup sweetener having a protein content of less than about 3.5%, the product being colloidal or non-filtratable.

9. The product of claim 8 wherein glucosidase and beta-amylase enzymes are employed in combination in the saccharification step to yield a saccharification product having at least about 70% solids with a composition of:

| | |
|---|---|
| Soluble complex carbohydrates | about 10 to 70% of solids; |
| Maltose | about 0 to 70% of solids; |
| Glucose | about 5 to 70% of solids; |
| Non-carbohydrate nutritional components | about 1 to 5% of solids; | and substantially no fiber.

10. The product of claim 9 wherein the starting material is selected as whole grain rice particles and the liquifaction, saccharification and clarification steps are selected to yield the rice syrup sweetener product having nutritional components comprising ash or minerals at about 0.1 to 0.6% of solids and protein and fat at about 1 to 3.5% of solids.

11. A rice syrup sweetener product characterized by substantial absence of a rice-like flavor while being colloidal or non-filtratable with a protein content of less than about 3.5% and at least about 70% total solids, balance essentially water, comprising:

| | |
|---|---|
| Soluble complex carbohydrates | about 10 to 70% of solids; |
| Maltose | about 0 to 70% of solids; |
| Glucose | about 5 to 70% of solids; |

12. The rice syrup sweetener product of claim 11 wherein non-carbohydrate nutritional components in the rice syrup sweetener product comprise ash or minerals at about 0.1 to 0.6% solids and protein and fat at about 1 to 3.5% of solids.

13. The rice syrup sweetener product of claim 12 being dried to substantially remove water and form a dried rice sweetener product.

14. The rice syrup sweetener product formed by a method comprising the steps of
    selecting as a starting material a whole grain rice and dividing it into particles of reduced size,
    liquifying the whole grain rice particles with an alpha-amylase enzyme in an aqueous medium substantially free from protease in an amount and for a period of time sufficient to form a liquid slurry,
    treating the liquid slurry with a beta-amylase enzyme in a saccharification step wherein at least about 1,000 BP° of beta-amylase enzyme per kilogram of whole grain rice particles are employed in the saccharification step and the reaction time for the saccharification step is limited to about three hours, the amount of beta-amylase enzyme and the reaction time being further selected to prevent development of off-flavors,
    clarifying the saccharification product to remove substantially all rice fiber to form a partially clarified product, and
    concentrating the partially clarified product to produce the rice syrup sweetener product from the whole grain rice.

15. The rice syrup sweetener product of claim 14 wherein the method further comprises the step of drying the rice syrup sweetener product to substantially remove water in order to form a dried rice syrup sweetener product.

* * * * *